United States Patent [19]

Burke

[11] Patent Number: 4,788,334

[45] Date of Patent: Nov. 29, 1988

[54] ACID ACCELERATED HYDROCARBOXYLATION

[75] Inventor: Patrick M. Burke, Wilmington, Del.

[73] Assignee: E. I. Du Pont de Nemours and Company, Wilmington, Del.

[21] Appl. No.: 943,310

[22] Filed: Dec. 10, 1986

[51] Int. Cl.$^4$ ............................................. C07C 51/14
[52] U.S. Cl. .............................. 562/522; 260/410.9 R; 560/204; 560/207
[58] Field of Search ............................... 560/204, 207; 260/410.9 R, 413; 562/522

[56] References Cited

FOREIGN PATENT DOCUMENTS 49674  4/1982  European Pat. Off. ............ 560/204
188209  7/1986  European Pat. Off. ............ 562/517

Primary Examiner—Werren B. Lone

[57] ABSTRACT

A process for the production of carboxylic acids by the hydrocarboxylation of olefinically unsaturated alkenes or esters using a rhodium catalyst, an iodide promoter, a solvent selected from the class consisting of methylene chloride, 1,2-dichloroethane, and $C_6$ to $C_9$ aromatic solvents, and an accelerator which is an acid having a pKa in the range of 4.2 to 5.2.

6 Claims, No Drawings

ACID ACCELERATED HYDROCARBOXYLATION

FIELD OF THE INVENTION

This invention relates to the hydrocarboxylation of olefinically unsaturated straight chain alkenes and esters.

BACKGROUND OF THE INVENTION

The hydrocarboxylation of olefinically unsaturated compounds using rhodium catalysts and iodide promoters in which the reactant is dissolved in a compatible solvent is disclosed in Craddock et al. U.S. Pat. No. 3,579,552.

The hydrocarboxylation of butadiene in methylene chloride using a rhodium catalyst and an iodide promoter is disclosed in U.S. Pat. No. 4,622,423.

SUMMARY OF THE INVENTION

The present invention is a process for the hydrocarboxylation of olefinically unsaturated straight chain compounds selected from esters and terminally unsaturated alkenes to form a mixture which contains more of the linear carboxylic acid than can be obtained by prior art processes. According to the present invention the olefinically unsaturated compound is dissolved in a solvent selected from the class consisting of methylene chloride, 1,2-dichloroethane and aromatic solvents having 6 to 9 carbon atoms, e.g., benzene, toluene, xylene, ethyl benzene; the solution is then mixed with carbon monoxide water, a rhodium catalyst, an iodide promoter, and an accelerator selected from the class consisting of aliphatic and aromatic acids having a pKa in the range of 4.2 to 5.2. The mixture is then reacted at a temperature of 50° to 300° C., and the resulting product contains linear acid in a high proportion.

DETAILED DESCRIPTION

The feedstock for the process of this invention is a linear olefinically unsaturated ester having 4 to 16 carbon atoms in the "acid portion" of the ester, e.g., in the formula

$$R_1CH=CH(CH_2)_n\overset{O}{\overset{\|}{C}}-OR_2$$

where n is 0 to 5, $R_1$ is H, $CH_3$ or $C_2H_5$ and $R_2$ is alkyl, or a linear terminally olefinically unsaturated alkene having 4 to 16 carbon atoms.

The reaction can be conducted over a reasonably wide temperature range, but relatively mild conditions are preferred. Acceptable yield is realized at temperatures in the range 100° to 220° C. and preferably 140° to 200° C. Temperatures above the upper end of the range result in a significant reduction in the conversion of the feedstock to the linear acid. At temperatures below the lower end of the range, the reaction is too slow to be economic.

Relatively moderate partial pressures of carbon monoxide, i.e., in the range 10 to 200 and preferably 13 to 20 atm are satisfactory. When the catalyst is a rhodium halide, the process may be carried out at a pressure in the range of 1 to 50 atmospheres.

The catalyst employed can be any rhodium complex that is free of interferring ligands particularly bidentate phosphine and nitrogen ligands. Rhodium complexes such as rhodium(III) chloride-$RhCl_3 \cdot 3H_2O$, rhodium-(III) iodide-$RhI_3$, rhodium carbonyliodide-$Rh(CO)_nI_3$ ($N=2-1$), rhodium(III) nitrate-$Rh(NO_3)_3 \cdot 2H_2O$, dodecacarbonyltetrarhodium(O)-$Rh_4(CO)_{12}$, acetylacetonatodicarbonylrhodium(I)-$Rh(CO)_2(C_5H_7O_2)$, chlorobis(ethylene)rhodium(I) dimer-$[Rh(C_2H_4)_2Cl]_2$, acetylacetonato(1,5-cyclooctadiene)-rhodium(I)-$Rh(C_8H_{12})(C_5H_7O_2)$, chlorocarbonylbis(triphenylphosphine)rhodium(I)-$RhCl(CO)(PPh_3)_2$, hexadecacarbonylhexarhodium(O)-$Rh_6(CO)_{16}$, tris-(acetylacetonato)rhodium-III)-$Rh(C_5H_7O_2)_3$, rhodium-(II)octonoate dimer-$Rh_2[CO_2(CH_2)_6CH_3]_4$, chlorodicarbonylrhodium(I) dimer-$[Rh(C))_2Cl]_2$, chloro(1,5-cyclooctadiene)rhodium(I) dimer-$[Rh(C_8H_{12})Cl]_2$, acetylacetonatobis(ethylene)rhodium(I)-$Rh(C_2H_4)_2(C_5H_7O_2)$ and rhodium(II)acetate dimer-$Rh_2(CO_2CH_3)_4$.

The concentration of catalyst is not critical but is usually maintained in the range 0.04–0.16% by weight of rhodium metal based upon the weight of the reaction medium. The catalyst must be promoted by iodide to achieve a satisfactory reaction rate. Hydrogen iodide is the preferred iodide source, but an alkyl iodide having 1–10 carbon atoms, e.g., methyl iodide, is a suitable promoter especially at the higher reaction temperature. Other suitable promoters include iodoethane, 1-iodobutane, 2-iodopropane, 1-iodopropane and iodoheptane. As believed apparent from the foregoing, the promoter and rhodium can be present in the same compound as in rhodium iodide. Generally the concentration of promoter is between 0.1 to 1.0% by weight iodide based upon the weight of the reaction medium and at a mole ratio to rhodium of at least 3.0/1.

The reaction is carried out in the presence of a solvent selected from the class consisting of methylene chloride, 1,2-dichloroethane, and $C_6$ to $C_9$ aromatic solvents. The amount of solvent employed can vary widely, e.g., 40 to 99 usually 60 to 99 and preferably 85 to 95% by weight based on the weight of the reaction mixtures.

In order to obtain the increased yield of the linear acid it is critical that the reaction be carried out in the presence of an accelerator selected from the class consisting of aliphatic and aromatic acids having a pKa in the range of 4.2 to 5.2. The acid should be present in the reaction mixture in an amount, on a molar basis, at least equal to the amount of the olefinically unsaturated compound, and the acid may be present in an amount at least 10 times that of the olefinically unsaturated compound. The preferred acids are $C_2$ to $C_5$ aliphatic carboxylic acids.

EXAMPLES

Example 1

A 300 ml Hastelloy-C mechanically stirred reactor was flushed with nitrogen and then with high purity carbon monoxide. The reactor was then charged with 150 ml of a methylene chloride solution containing hexene-1 (12.6 g; 150 mmoles), acetic acid (18.0 g; 300 mmoles), methanol (0.48 g), methyl iodide (2.13 g; 15 mmoles) and o-dichlorobenzene (5.0 g; internal standard for gas chromatographic analysis). The reactor was pressured with CO to a pressure of 200 psi and then heated to 170°. The hydrocarboxylation reaction was initiated by injecting, from a 15 ml cylinder connected to the reactor, a solution containing 0.4 g $RhCl_3 \cdot 3H_2O$ (1.5 mg-atom rhodium) in 6 ml water. The reactor pressure was then adjusted to exactly 400 psi by means of a regulator valve. The uptake of CO, and hence the carbonylation rate, was monitored by measuring the pressure drop in the reservoir by means of a pressure transducer. The pressure drop was related to moles of CO uptake by means of a previous flow calibration.

Uptake of CO was 76 psi. It was essentially complete after 3 hours. The rate, based on CO uptake, was kinetically first order in hexene-1 and the rate constant was $25.3 \times 10^{-3}$ min$^{-1}$.

After 6.5 hours, the reactor was cooled to 20°. The CO was slowly vented through a control valve. The product solution was discharged from the reactor and the reactor was washed with 200 ml methanol at 100° under pressure and then with 150 ml methanol at ambient temperature. The product and wash solutions were combined and analyzed by gas chromatography as their methyl esters.

The analysis showed 68.4% n-heptanoic acid and 9.5% 2-methylhexanoic acid, based on the 1-hexene added. The selectivity to the linear acid was then 87.8%.

Control Example 1

The above experiment was repeated except that the acetic acid accelerator was omitted.

Uptake of CO was only 8 psi after 5 hours. The first order rate constant was $0.58 \times 10^{-3}$ min$^{-1}$.

The reaction was stopped by cooling to room temperature after 5 hours. Analysis of the product as the methyl esters showed only 9.3% n-heptanoic acid and 2.1% 2-methylhexanoic acid (81.6% linearity).

Thus, the presence of the acetic acid (per Example 1) increased the rate by a factor of 43.6.

Examples 2 to 5

Example 1 was repeated except that the amount of acetic acid was varied. The results obtained are summarized in Table 1.

The data show that the acceleration effect of acetic acid on the hydrocarboxylation rate increases with its concentration. Although highest rates are obtained in neat acetic acid (Example 5), the selectivity to the linear isomer ("linearity") is substantially lower compared with reactions run in methylene chloride containing solvents.

TABLE 1

| | Grams Acetic Acid | Mole Ratio* | Yield C$_7$ Acids | Linearity | Rate (k × 10$^3$ min$^{-1}$) |
|---|---|---|---|---|---|
| Example 2 | 12.6 | 1.0 | 67.4 | 77.1 | 9.8 |
| Example 3 | 36.0 | 4.0 | 79.4 | 81.4 | 27.0 |
| Example 4 | 72.0 | 8.0 | 72.0 | 78.1 | 36.6 |
| Example 5 | 130 | — | 76.6 | 65.7 | 61.6 |

Conditions: As in Example 1, except that the amount of acetic acid was varied as is shown in Col. 2
*moles acetic acid per mole hexene-1

Example 6

The experiment in Example 1 was repeated except that the acetic acid was replaced with 18.3 g (150 mmoles) of benzoic acid. Uptake of CO (64 psi) was complete in about 2 hours. The first order rate constant for the reaction was $11.6 \times 10^{-3}$ min$^{-1}$.

Analysis of the product showed 87.2% C$_7$ carboxylic acids based on the hexene-1 charged. The linear selectivity was 78.8%.

Example 7

The experiment in Example 1 was repeated, except that the acetic acid was replaced with 15.3 g (150 mmoles) of trimethylacetic acid (2,2-dimethylpropionic acid).

Uptake of CO (75 psi) was complete in about 1.5 hours. The first order rate constant was $21.1 \times 10^{-3}$ min$^{-1}$ and the yield of C$_7$ carboxylic acids was 90%. The linear selectivity was 78.2%.

Example 8

The experiment in Example 1 was repeated, except that the hexene-1 was replaced with an equivalent amount (17.1 g; 150 mmoles) of methyl-4-pentenoate, and the amount of acetic acid was reduced to 9.0 g (150 mmoles). Uptake of CO (75 psi) was complete in about 4 hours. The first order rate constant was $15.2 \times 10^{-3}$ min$^{-1}$. Analysis of the reaction mixture before diluting with methanol showed that the major product was monomethyl adipate. After esterification with methanol, the analysis showed 66% adipic acid, 13.4% methylglutaric acid (as dimethyl esters) and 16.8% γ-valerolactone (linearity, 83.1%).

Control Example 8A

The experiment in Example 8 was repeated, except that the acetic acid was omitted. After 5 hours, uptake of CO was only 28 psi. The first order rate constant (after a 1-hour induction period) was only $1.5 \times 10^{-3}$min$^{-1}$. Analysis of the product as the methyl esters showed 31% adipic acid, 6.2% α-methylglutaric acid, 22.8% 3-pentenoic acid and 21.8% recovered 4-pentenoic acid.

Example 9

The experiment in Example 8 was repeated, except that the methyl-4-pentenoate was replaced with methyl-3-pentenoate (17.1 g).

Uptake of CO (70 psi) was essentially complete in 5 hours and the first order rate constant was $7.5 \times 10^{-3}$min$^{-1}$. Analysis of the product as the methyl esters showed 48.3% adipic acid, 21.4% α-methylglutaric acid, 4.3% ethylsuccinic acid and 9.3% γ-valerolactone (linearity: 65.3%).

Control Example 9A

The experiment in Example 9 was repeated except that the acetic acid was omitted.

After 5 hours, uptake of CO was only about 15 psi. The rate constant was $1.1 \times 10^{-3}$min$^{-1}$. Analysis of the product as the methyl esters showed 76.6% recovered 3-pentenoic acid, 15.1% adipic acid, and 5.3% α-methylglutaric acid (linearity 73.9%).

I claim:

1. A process for the hydrocarboxylation of an olefinically unsaturated straight chain compound selected from the class consisting of linear olefinically unsaturated esters having the formula:

wherein n is 0 to 5, R$_1$ is H, CH$_3$ or C$_2$H$_5$ and R$_2$ is alkyl, and terminally unsaturated alkenes having 4 to 16 carbon atoms to form a mixture containing an increased amount of linear carboxylate acid, which comprises dissolving said compound in a solvent selected from the class consisting of methylene chloride; 1,2-dichloroethane and aromatic solvents having 6 to 9 carbon atoms, mixing the thus formed solution with carbon monoxide, water, rhodium catalyst, iodide promoter and an accelerator selected from the class consisting of aliphatic and aromatic acids having a pKa in the range of 4.2 to 5.2 in an amount at least equal, on a molar basis, to the amount of olefinically unsaturated straight chain compound, and reacting the mixture at temperature of from 50° to 300° C. to form linear carboxylic acid.

2. The process of claim 1 in which the olefinically unsaturated straight chain compound is terminally unsaturated.

3. The process of claim 2 in which the catalyst is a rhodium halide and the process is carried out at a pressure in the range of 1 to 50 atmospheres.

4. The process of claim 2 in which the terminally olefinically unsaturated compound is an alkene.

5. The process of claim 2 in which the olefinically unsaturated straight chain compound is methyl-4-pentenoate.

6. The process of claim 1 in which the olefinically unsaturated straight chain compound is methyl-3-pentenoate.

* * * * *